United States Patent [19]

Ikada et al.

[11] Patent Number: 4,844,067
[45] Date of Patent: Jul. 4, 1989

[54] SUCROSE FATTY ACID ESTER COATED SUTURE

[75] Inventors: Yoshito Ikada; Shokyu Gen, both of Uzi; Tatsuya Kawai, Hiroshima; Takashi Matsuda, Hiroshima, all of Japan

[73] Assignees: Japan Medical Supply Co., Ltd.; Gunze Co., Ltd.; Bio Materials Universe, Inc., all of Japan; part interest to each

[21] Appl. No.: 153,996

[22] Filed: Feb. 9, 1988

[30] Foreign Application Priority Data

Feb. 19, 1987 [JP] Japan .................. 62-37475
Apr. 2, 1987 [JP] Japan .................. 62-81380

[51] Int. Cl.⁴ .............................. A61L 17/00
[52] U.S. Cl. ..................... 128/335.5; 427/2
[58] Field of Search ............ 128/335.5, 334; 623/11, 623/13, 66; 524/306; 536/119; 427/2

[56] References Cited

U.S. PATENT DOCUMENTS

| | | | |
|---|---|---|---|
| 3,883,901 | 5/1975 | Coquard et al. | 128/335.5 X |
| 3,942,532 | 3/1976 | Hunter et al. | 128/335.5 |
| 4,027,676 | 6/1977 | Mattei | 128/335.5 |
| 4,047,533 | 9/1977 | Perciaccante et al. | 128/335.5 |
| 4,105,034 | 8/1978 | Shalaby et al. | 128/335.5 |
| 4,185,637 | 1/1980 | Mattei | 128/335.5 |
| 4,201,216 | 5/1980 | Mattei | 128/335.5 |
| 4,397,951 | 8/1983 | Taki et al. | 435/218 X |
| 4,426,477 | 1/1984 | Yasumatsu et al. | 524/306 |
| 4,532,929 | 8/1985 | Mattei et al. | 128/335.5 |
| 4,711,241 | 12/1987 | Lehmann | 128/334 X |

FOREIGN PATENT DOCUMENTS 6171058 11/1986 Japan .
1418524 12/1975 United Kingdom .
1583390 1/1981 United Kingdom .

Primary Examiner—Richard J. Apley
Assistant Examiner—Alan W. Cannon
Attorney, Agent, or Firm—Kramer, Brufsky & Cifelli

[57] ABSTRACT

A suture coating composition comprising a sucrose fatty acid ester and sutures coated therewith whereby said sutures exhibit improved smoothness in tie-down properties and knotting can be readily accomplished using said suture.

8 Claims, 1 Drawing Sheet

SUCROSE FATTY ACID ESTER COATED SUTURE

FIELD OF THE INVENTION

The present invention relates to suture coating compositions comprising sucrose fatty acid esters and improved sutures coated therewith, which sutures exhibit improved tie-down properties.

BACKGROUND OF THE INVENTION

Suture materials are classified as either absorbable or nonabsorbable, and are considered to be absorbable if they disappear from the sewn tissue within a year after surgery. Most absorbable suture materials disappear within shorter periods. Absorbable suture materials are preferred for applications in which the sewn tissues after healing should hold together without suture reinforcement and in which a nonabsorbable suture may provide the possibility of an adverse bodily reaction over an extended period of time.

The most commonly used absorbable suture materials are lactide homopolymer, glycolide homopolymer, copolymers of lactide and glycolide, and chitin. These monofilament synthetic absorbable suture materials are generally stiff and, therefore, these synthetic absorbable sutures are usually employed in a braided, multifilament construction in order to obtain the desired flexibility and softness. Silk, nylon and polyester are also employed in a braided construction as nonabsorbable suture materials.

Whether absorbable or nonabsorbable, such multifilament sutures show a certain degree of undesirable roughness or grabbiness in what has been termed their "tie-down" performance, i.e., the ease and smoothness of sliding a knot down the suture into place. Therefore, in order to improve the sliding properties of the sutures, surface coatings have been employed.

Sutures coated with beeswax to improve the living tissue absorption rate of the sutures is disclosed in Japanese Patent Laid-Open No. 59-181160(1984). Sutures coated with lubricious copolymers which contain polyoxyethylene blocks and polyoxypropylene blocks in order to improve the tie-down properties are disclosed in Japanese Patent Publication No. 61-30586(1986) and in U.S. Pat. Nos. 4,047,533 and 4,043,344.

Comparison of coated sutures with uncoated sutures reveals that the coated sutures exhibit improved sliding properties to a certain degree, but the improvement and effectiveness is insufficient. In addition, because the surface coating directly contacts living tissue, a coating material which is safe and nontoxic has been sought.

An object of the present invention is to provide sutures having good tie-down properties.

Another object of the present invention is to provide sutures coated with safe and nontoxic coating materials.

BRIEF DESCRIPTION OF THE DRAWINGS

Further objects and benefits of the present invention, in addition to the foregoing, are more readily understood by reference to the drawings wherein.

DETAILED DESCRIPTION OF THE INVENTION

Figure 1:
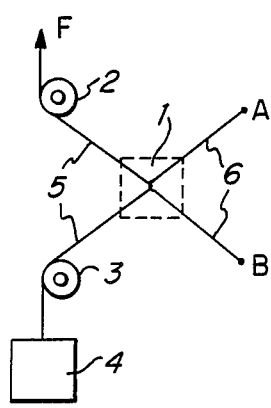
FIG. 1 is a diagrammatic representation of a tensile tester for determining tie-down performance of the sutures.

The sucrose fatty acid esters used in the present invention are esters comprising sucrose, a fatty acid and an ester selected from the group consisting of monoesters, diesters, polyesters, and mixtures thereof. The synthesis of sucrose fatty acid esters is well known by those skilled in the art and the method employed herein is disclosed in U.S. Pat. No. 3,792,041. The esterification rate and hydroxyl value are inversely proportional to each other. When the hydroxyl value is high, the esterification rate is low, while conversely, when the hydroxyl value is low, the esterification rate is high. Accordingly, when measuring the hydroxyl value, the esterification rate can be concurrently obtained. Preferably, the hydroxyl value is about 130 or less.

Stearic acid, palmitic acid, lauric acid and myristic acid are the preferred fatty acids to be employed, either alone or as mixtures thereof. Fatty acid mixtures of the foregoing higher fatty acids in combination with lower fatty acids, such as acetic acid and butyric acid, can also be used.

Sucrose fatty acid esters have been widely used heretofore for various purposes, mainly as emulsifiers, frothers, and dispersion mediums for foodstuffs. Accordingly, it would appear to be nontoxic and acceptable as a coating composition for sutures.

Various methods of coating sutures are available. In the most common coating method, the liquified sucrose fatty acid ester is applied to the suture surface and solidified thereafter. The coating is liquified by dissolving the coating in a solvent and solidification is accomplished by volatilizing the solvent. The coating solution can be applied to the suture by any suitable process such as, moving the suture through a receptacle containing the solution or past a brush wetted with the solution. Water, methanol, ethanol, isopropanol, acetone, hexane, methylethylketone or ethyl acetate can be used as the solvent.

The sucrose fatty acid ester can also be applied to the suture as a melt, and in such a case, solidification takes place by cooling. As the sucrose fatty acid ester has a melting point ranging from about 45° C. to 65° C., it can readily be melted by heat. Application of the coating as a melt has the following advantages: (1) the suture material does not contact the solvent and thus, there is no risk that the suture material is being denatured or decomposed from contact with the solvent; and (2) it is not necessary to volatilize the solvent after coating.

Alternatively, coating can be accomplished using solid sucrose fatty acid esters. In this case, the coating can be applied to the suture by passing the suture over or between solid blocks of the sucrose fatty acid ester, which is thereby transferred to the surface of the suture by rubbing.

After the suture material is spun and coated, it is then braided. Alternatively, the suture is first braided into a multifilament and then directly coated. The suture can be coated one or more times.

The coating thickness is dependent upon the intended use of the suture and its determination is within the skill of the art.

Preferably, the coating thickness is as thin as possible for optimum operability, from cost aspects and in order to maintain the desired tie-down properties. Suitable living tissue absorbable suture materials include homopolymer and copolymers of lactide, glycolide, β-hydroxybutylcarboxylic acid, β-propiolactone, γ-butyrolactone, γ-valero-e-methylbutyrolactone, δ-valerolactone, ξ-caprolactone, chitin, and the like. Suitable living tissue nonabsorbable suture materials include silk, nylon or polyester.

Figure 2:
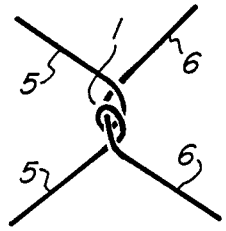
FIG. 2 is an enlarged perspective view of the knot state illustrated in FIG. 1.

The improved tie-down properties of the suture of the present invention can be shown qualitatively and/or organoleptically by comparing the feel of the coated and the uncoated sutures during the tie-down procedure. Furthermore, the improvement can also be shown quantitatively by the test described in FIG. 1. To perform the tie-down procedure, two sutures, 5 and 6, are intertwined as shown in FIG. 2, with one of them fixed at Point A and Point B. One end of the other suture is passed around pulley 3 and attached to weight 4 while placing force (F) on the other end. The weight which will be used to provide tension preferably weighs between about 50 and about 100 grams.

EXAMPLE 1

A braided multifilament glycolide homopolymer absorbable suture material was used. Fatty acid composed of stearic acid, palmitic acid and acetic acid reacted with sucrose was used as the sucrose fatty acid ester, wherein the hydroxyl value is less than 20. Since the melting point of the sucrose fatty acid ester is rather low, i.e., in the range of 44° to 50° C., the following coating method was specially employed.

Figure 3:
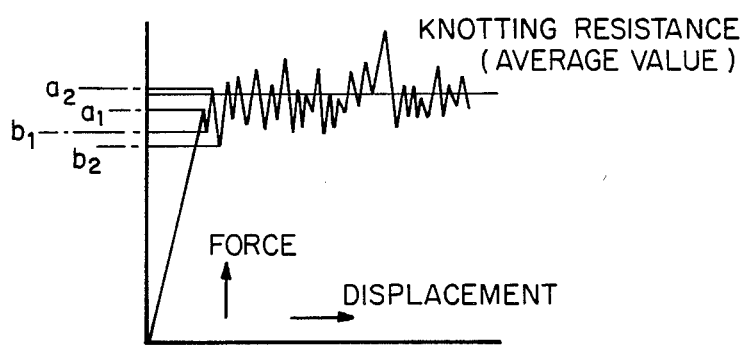
FIG. 3 is a representation of a typical trace of an oscillographic recorder used in the tie-down performance test.

First, the sucrose fatty acid ester was heated to 50° C. to melt it, the testing suture was then drawn through a bath of this solution for ten seconds. Thereafter, the surface was lightly wiped with gauze. Then, the suture was placed in a thermostatic oven at a temperature of 60° C. for 30 minutes. The suture was then wiped with gauze and the coating solidified by cooling. The thus prepared coated suture was tested as described in FIG. 1 to determine its tie-down properties. FIG. 3 is a representation of a typical trace of an oscillographic recorder. The difference in the level between a1 and b1 is the roughness value. The final roughness value measured is the roughness average value which is the difference of the maximum value and the minimim value next to each other; for (example, (a1−b1) +. . . + (an−bn)/n. In other words, the lower the knotting resistance is, the smaller the force required, and the smaller the roughness value is, and the smoother the tie-down accomplished. The results are shown in Table 1.

EXAMPLE 2

The same suture material as was used in Example 1 was used, but a fatty acid composed of stearic acid and palmitic acid reacted with sucrose, with a hydroxyl value ranging from 80 to 130 was used as sucrose fatty acid ester. Since the melting point of this sucrose fatty acid ester is in the range of between 60° and 66° C., the following coating method was employed.

First, the sucrose fatty acid ester was heated to 70° C. and melted, thereafter the testing suture was drawn through a bath of this solution for ten seconds and then the surface lightly wiped with gauze. Then, the suture was placed in the thermostatic oven at a temperature of 70° C. for 30 minutes and thereafter, its surface is again lightly wiped with gauze and solidified by cooling. The coated suture, thus prepared, was tested as described in Example 1, to determine the tie-down properties. There was no change in the roughness properties as shown in FIG. 3. The results are shown in Table 1.

EXAMPLE 3

The same suture material as was used in Example 1 was used, and a fatty acid composed of stearic acid, palmitic acid and acetic acid reacted with sucrose with a hydroxyl value of less than 20 was used as the sucrose fatty acid ester. Using ethyl acetate as the solvent, 50 grams of the sucrose fatty acid ester was melted by dissolving it into 1 liter of ethyl acetate in a water-bath maintained at 60° C. The suture was then placed in the foregoing solution while maintaining the solution temperature at 60° C. for 30 seconds and thereafter, the suture was dried under the atmospheric condition of −76 cmHg and the temperature of 60° C. for 30 minutes, and solidified by cooling. After the change in weight was measured, it was found that sucrose fatty acid ester pick-up was 5%. The thus coated suture was tested using the same procedure as described in Example 2 to determine the suture's tie-down properties. The results of the roughness test were similar to those in FIG. 3. The results are shown in Table 1.

TABLE 1

| | 50 Gram Load | |
| --- | --- | --- |
| | Knotting Resistance (Average Value) | Roughness Value |
| Uncoated suture | 220 g | 112 g |
| Example 1 | 210 g | 22 g |
| Example 2 | 210 g | 10 g |
| Example 3 | 180 g | 10 g |
| Commercially Available Coated Suture | 200 g | 52 g |

| | 100 Gram Load | |
| --- | --- | --- |
| Uncoated suture | 410 g | 123 g |
| Example 1 | 330 g | 19 g |
| Example 2 | 350 g | 14 g |
| Example 3 | 330 g | 20 g |
| Commercially Available Coated Suture | 390 g | 92 g |

The test results of the commercially available coated absorbable suture (Brand name=DEXON PLUS, manufactured by Davis and Geck) was also included for comparative purposes. As can be seen from the foregoing data, the suture of the present invention exhibits less knotting resistance, while at the same time, demonstrating a marked improvement in roughness value. The suture of the present invention also exhibited superiority over the commercially available coated suture.

What is claimed is:

1. A suture coated with a composition consisting essentially of sucrose fatty acid ester.

2. A suture according to claim 1 wherein said sucrose fatty ester comprises a fatty acid selected from the group consisting of stearic acid, palmitic acid, lauric acid, myristic acid, and mixtures thereof.

3. A suture according to claim 1 wherein said sucrose fatty acid ester comprises an ester selected from the group consisting of monoester, diester, polyester and mixtures thereof.

4. A suture according to claim 3 wherein said sucrose fatty acid ester exhibits a hydroxyl value of less than about 130.

5. A suture according to claim 6 wherein said sucrose fatty acid ester comprises a fatty acid selected from the group consisting of stearic acid, palmitic acid, lauric acid, myristic acid and mixtures thereof in admixture with acetic acid or butyric acid.

6. A suture according to claim 1 wherein said suture comprises homopolymer and copolymers of lactide, glycolide, 8-hydroxybutylcarboxylic acid, $\beta$-propiolactone, $\gamma$-butyrolactone, $\gamma$-valero-3-methylbutyrolactone, $\delta$-valerolactone, chitin, and $\xi$-caprolactone.

7. A suture according to claim 6 wherein said suture comprises homopolymers or copolymers of glycolide.

8. A suture according to claim 1 wherein said suture comprises silk, nylon or polyester.

* * * * *

UNITED STATES PATENT AND TRADEMARK OFFICE
CERTIFICATE OF CORRECTION

PATENT NO. : 4,844,067

DATED : July 4, 1989

INVENTOR(S) : Ikada et al.

It is certified that error appears in the above-identified patent and that said Letters Patent is hereby corrected as shown below:

IN THE CLAIMS

In claim 5, column 5, line 1, delete "6" and insert -- 1 -- in lieu thereof.

Signed and Sealed this

Twenty-fourth Day of April, 1990

Attest:

HARRY F. MANBECK, JR.

*Attesting Officer*     *Commissioner of Patents and Trademarks*